(12) United States Patent
Djajadiningrat

(10) Patent No.: US 10,984,914 B2
(45) Date of Patent: Apr. 20, 2021

(54) CPR ASSISTANCE DEVICE AND A METHOD FOR DETERMINING PATIENT CHEST COMPRESSION DEPTH

(71) Applicant: KONINKLIJKE PHILIPS N.V., Eindhoven (NL)

(72) Inventor: Johan Partomo Djajadiningrat, Utrecht (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 186 days.

(21) Appl. No.: 16/099,015

(22) PCT Filed: May 6, 2017

(86) PCT No.: PCT/EP2017/060847
§ 371 (c)(1),
(2) Date: Nov. 5, 2018

(87) PCT Pub. No.: WO2017/191324
PCT Pub. Date: Nov. 9, 2017

(65) Prior Publication Data
US 2019/0133879 A1 May 9, 2019

(30) Foreign Application Priority Data
May 6, 2016 (EP) .................................... 16168572

(51) Int. Cl.
*G16H 70/20* (2018.01)
*G16H 20/30* (2018.01)
(Continued)

(52) U.S. Cl.
CPC ............ *G16H 70/20* (2018.01); *A61H 31/005* (2013.01); *G16H 20/30* (2018.01); *G16H 30/40* (2018.01);
(Continued)

(58) Field of Classification Search
CPC .... A61H 31/00–008; A61H 2201/5028; A61H 2201/5064; A61H 2201/5092;
(Continued)

(56) References Cited

U.S. PATENT DOCUMENTS 10,335,346 B2 * 7/2019 Centen .................. G06T 7/269
10,420,701 B2 * 9/2019 Freeman ............ H04N 5/23238
(Continued)

FOREIGN PATENT DOCUMENTS

WO 2011011633 A2 1/2011
WO 2012063163 A1 5/2012

OTHER PUBLICATIONS

Grimaldi et al: "Photoplethysmography Detection by Smartphone's Videocamera"; The 6th IEEE International Conference on Intelligent Data Acquisition and Advanced Computing Systems: Technology and Applications, Sep. 2011, Prague, Czech Republic; pp. 488-491.
(Continued)

*Primary Examiner* — Rachel T Sippel
*Assistant Examiner* — Kelsey E Baller

(57) ABSTRACT

A Cardiopulmonary resuscitation assistance device is used by a Rescuer when administering Cardiopulmonary resuscitation to a patient. Using the rescuer vital signs, image subsection from a patient facing camera can be identified that comprise the rescuer's hands. Having correctly identified the image subsections comprising the rescuer's hands
(Continued)

the chest compression depth and frequency can be derived from the patient facing camera by tracking the distance between the patient facing camera and the rescuer's hands.

14 Claims, 3 Drawing Sheets

(51) Int. Cl.
 *G16H 30/40* (2018.01)
 *A61H 31/00* (2006.01)
(52) U.S. Cl.
 CPC .... *A61H 31/007* (2013.01); *A61H 2201/5028* (2013.01); *A61H 2201/5064* (2013.01); *A61H 2201/5092* (2013.01)
(58) Field of Classification Search
 CPC ........ A61H 2201/5094; A61H 2230/04; A61H 2230/08; G06F 19/3481; G06T 7/50; G06T 7/52; G06T 7/596; G06T 7/20; G06K 2009/0093; G06K 9/0039
 See application file for complete search history.

(56) References Cited

U.S. PATENT DOCUMENTS

| | | | | |
|---|---|---|---|---|
| 10,667,988 | B2* | 6/2020 | Freeman | A61N 1/3993 |
| 2013/0077823 | A1* | 3/2013 | Mestha | A61B 5/0077 |
| | | | | 382/103 |
| 2014/0241588 | A1 | 8/2014 | Rocque | |
| 2014/0342331 | A1 | 11/2014 | Freeman | |
| 2015/0170546 | A1 | 6/2015 | Kirenko | |
| 2015/0236740 | A1* | 8/2015 | De Haan | A61B 5/6887 |
| | | | | 375/340 |
| 2017/0273864 | A1* | 9/2017 | Kaufman | G16H 40/67 |
| 2019/0282324 | A1* | 9/2019 | Freeman | A61B 34/25 |

OTHER PUBLICATIONS

Verkruysse et al: "Remote Plethysmographic Imaging Using Ambient Light"; Opt Express, 2008, vol. 16 (26), pp. 21434-21445.
Wieringa et al: "Contactless Multiple Wavelengt5h Photoplethysmographic Imaging: A First Step Toward "SpO2 Camera" Technology"; Annals of Biomedical Engineering, vol. 33, No. 8, Aug. 2005, pp. 1034-1041.

* cited by examiner

CPR ASSISTANCE DEVICE AND A METHOD FOR DETERMINING PATIENT CHEST COMPRESSION DEPTH

Cross-Reference to Prior Applications

This application is the U.S. National Phase application under 35 U.S.C. § 371 of International Application No. PCT/EP2017/060847, filed on May 6, 2017, which claims the benefit of European Patent Application No.16168572.2, filed on May 6, 2016. These applications are hereby incorporated by reference herein.

FIELD OF THE INVENTION

This invention relates to a cardiopulmonary resuscitation assistance device for use by a rescuer device when administering cardiopulmonary resuscitation to a patient, the cardiopulmonary resuscitation assistance device comprising a patient facing camera, an image processing unit arranged to distinguish an image subsection in images provided by the patient facing camera comprising a rescuer body part, a data processor arranged to derive patient chest compression depth from the distinguished image subsection using a distance measurement between the camera and the image subsection performed by the camera, and a display arranged to provide cardiopulmonary resuscitation information based on the derived patient chest compression depth to the rescuer.

BACKGROUND OF THE INVENTION

Cardiopulmonary resuscitation is an emergency procedure performed in an effort to manually preserve intact brain function until further measures are taken to restore spontaneous blood circulation and breathing in a person in cardiac arrest. Cardiopulmonary resuscitation involves chest compressions at least 5 cm (2 inches) deep and at a rate of at least 100 per minute in an effort to create artificial circulation by manually pumping blood through the heart. Current recommendations place emphasis on high-quality chest compressions over artificial respiration. A simplified cardiopulmonary resuscitation method involving chest compressions only is recommended for untrained rescuers. Compression-only (hands-only or cardio cerebral resuscitation) cardiopulmonary resuscitation is a technique that involves chest compressions without artificial respiration. It is recommended as the method of choice for the untrained rescuer or those who are not proficient as it is easier to perform and instructions are easier to give over the phone. Audible and visual prompting may improve the quality of cardiopulmonary resuscitation and prevent the decrease of compression rate and depth that naturally occurs with fatigue, and to address this potential improvement, a number of devices have been developed to help improve cardiopulmonary resuscitation technique.

In order to assist a rescuer applying cardiopulmonary resuscitation on a patient a measure of depth of compressions of the patient's chest, and a frequency of compressions of the patient's chest. Visual and/or audible feedback may be provided to the user by comparing calculated values representative of the cardiopulmonary resuscitation performance with predetermined target values. E.g. the user may be informed to increase speed in case the cardiopulmonary resuscitation is performed too slowly.

Such a cardiopulmonary resuscitation assistance device is known from WO2011011633 where a camera is used to determine the chest compression depth during cardiopulmonary resuscitation. In order to determine the image subsection whose depth changes best represent the actual chest compression depth of the patient the hands of the Rescuer have to be identified in the image. As in many cases both the patient's chest and Rescuer's hands will be bare skinned it will be very difficult to distinguish the cardiopulmonary resuscitation rescuer's hands from the patient's chest. When a first responder gives cardiopulmonary resuscitation using the recommended interlocking hands grip, the grip makes it difficult for a computer vision system to recognize the hands as hands. If the image processing software is not able to identify the rescuer's hand position accurately it may identify the wrong image subsection to track and the resulting chest compression depth derived from this wrongly selected image are is inaccurate and the instructions given to the Rescuer will consequently be incorrect which in a life threatening situation is unacceptable.

SUMMARY OF THE INVENTION

It is an objective of the present invention to provide a cardiopulmonary resuscitation assistance device that can accurately determine the image subsection to be tracked for determining chest compression depth.

To achieve this objective the cardiopulmonary resuscitation assistance device comprises a rescuer vital signs detector and the data processor is arranged to derive a rescuer vital sign information from the Rescuer vital sign detector and the image processing unit is arranged to distinguish an image subsection from images captured by the patient facing camera comprising the rescuer body part by matching vital sign information derived from image subsections with rescuer vital sign information derived from the Rescuer vital sign detector.

Using differences in vital signs between the patient and rescuer allows the accurate determination of which image subsections comprise patient body parts as these will have vital signs differing from the vital signs of the rescuer and which images areas comprise a body part of the rescuer as in these image subsections the detected vital signs will match the vital sign information obtained from the rescuer's vital sign detector.

As only the image subsection where a rescuer body part is present can represent the chest compression depth accurately, all other areas can be excluded from consideration. This leads to a greatly simplified decision process for selecting which image subsection to track the depth and thus avoiding the selection of image subsections leading to incorrect chest compression depth and compression frequency determinations.

In an embodiment the rescuer body part to be distinguished is a hand of the Rescuer.

The hands typically apply the pressure to the patient's chest and the up and down movement accurately reflect the chest compression depths as the hands are in constant contact with the chest during cardiopulmonary resuscitation. Normally it is hard to distinguish the hands of the rescuer because of the complex shape caused by the overlapping hands. Also, when the cardiopulmonary resuscitation is applied to a bare chested patient the subtle differences in skin tones may make distinguishing shapes fundamentally difficult. By selecting an image subsection comprising only rescuer vital sign information the hands of the rescuer can easily be identified and determination of shapes and problems with subtle skin tone differences no longer exist.

In an embodiment the patient body part to be distinguished is a chest of the patient.

Knowing that an image subsection covers the patient's chest helps excluding this area as these areas are not the areas receiving the pressure and the observed compression depth will not accurately reflect the chest compression depth as these are not the areas receiving the pressure from the rescuer's hands.

In a further embodiment the image processing unit is further arranged to determine a chest compression depth using the distinguished body part of the rescuer.

Once the hands of the rescuer have been identified in the image they can be tracked and the changes, i.e. variations, in distance to the patient facing camera worn by the rescuer for instance as a head mounted camera will reflect the chest compression depth.

Various methods to determine the distance/depth from the camera to the image subsection are currently known and can be used.

In a further embodiment of the cardiopulmonary resuscitation assistance device the rescuer vital sign detector is a Rescuer facing camera, and where the image processing unit is arranged to derive rescuer vital sign information from images provided by the rescuer facing camera.

Having a rescuer facing camera allows the image processor, like when determining vital signs from image subsections in images received from the patient facing camera, determine the rescuer's vital signs from image subsections of images received from the rescuer facing camera. As the rescuer facing camera images will not have any image subsections comprising patient body parts, the vital signs obtained from the rescuer facing camera can be used to reliably identify rescuer body parts in the patient facing camera images. The patient facing camera is a forward facing camera and the rescuer facing camera is a rear facing camera.

In a further embodiment of the cardiopulmonary resuscitation assistance device the image processing unit is arranged to correct the chest compression depth using depth information obtained from images from the rescuer facing camera.

As the rescuer's head can move during cardiopulmonary resuscitation due to application and release of pressure to the patient's chest the variation in distance between the patient facing camera and the patient's chest doesn't always accurately reflect the actual chest compression depth. As the rescuer facing camera can determine the depth between the rescuer's head and stationary objects behind the rescuer, it can detect changes in this depth using distance measurements between the rescuer facing camera and the stationary object and compensate the chest compression depth determined using the patient facing camera using the depth changes determined using the rescuer facing camera.

A method for assisting a rescuer device when administering cardiopulmonary resuscitation to a patient, the method comprises the steps of obtaining images of the patient's chest are using a patient facing camera, processing the obtained images to distinguish an image subsection comprising a rescuer body part, deriving patient chest compression depth from the distinguished image subsection, and displaying cardiopulmonary resuscitation information based on the derived patient chest compression depth to the rescuer characterized in that the method further comprises the steps of detecting rescuer vital sign information, distinguish an image subsection from images captured by the patient facing camera comprising the rescuer body part by matching vital sign information derived from image subsections with rescuer vital sign information.

It is known how to detect vital signs of a person in a sequence of images as in a video stream.

Verkruysse et al., "Remote plethysmographic imaging using ambient light", Optics Express, 16 (26), 22 Dec. 2008, pp. 21434-21445 demonstrates that photoplethysmography signals can be measure remotely on the human face with normal ambient light as the source and a simple digital, consumer-level photo camera in movie mode. After setting the camera in movie mode, volunteers were asked to sit, stand or lie down to minimize any movements. Color movies were saved by the camera and transferred to a personal computer. Pixel values for the red, green and blue channels were read for each movie frame, providing a set of $PV(x,y,t)$, where x and y are horizontal and vertical positions, respectively and t is time corresponding to the frame rate. Using a graphic user interface, regions of interest (ROI) were selected in a still (selected from the movie) and the raw signal $PV\ raw(t)$ was calculated as the average of all pixel values in the ROI. Fast Fourier Transforms were performed to determine the power and phase spectra.

Wieringa F. et al.: "Contactless multiple wavelength photoplethysmographic imaging: A first step toward SpO2 camera technology" Annals of Biomedical Engineering, Kluwer Academic Publishers—Plenum Publishers, NE, Vol. 33, No. 8, 1 Aug. 2005, pages 1034-1041 discloses a method of acquiring heartbeat-related spatially resolved plethysmographic signals at multiple wavelengths using a remote camera.

Detection of vital signs can be achieved using an apparatus for detecting subjects on the basis of a vital sign, comprising: an image detection unit that detects radiation from a field of view and that provides image data from the field of view, a detection unit that defines image sections in the image data and that detects movement pattern in the different image sections, an identification unit that identifies vital signs in the different image section on the basis of the movement pattern, and an analysis unit that analyses the image data, wherein the analysis unit detects the different subjects in the field of view on the basis of a spatial separation of the image sections or of groups of image sections in which the vital signs are identified.

Analyzing information based on pixel data of a plurality of image parts in at least one of the images, where each image part includes at least one image point, can be conducted automatically, as can clustering those parts determined to have similar characteristics. This makes it suitable for unsupervised execution. Selecting contiguous parts determined to have similar characteristics results in the determination of a region of the image with homogeneous characteristics. If these characteristics are similar according to an analysis in the spatial domain, a better selection of a homogeneous zone which will form the measurement zone can be made. Even if the body part corresponding to the measurement zone does not remain exactly in position throughout the sequence of images, the pixel intensities in the measurement zone will not vary appreciably due to such variations in position. This improves the quality of the spectrum of signal corresponding to the time-varying value of the combination of pixel values at at least a number of the image points, so that reliable identifications of signal peaks corresponding to heart beat or breathing rate can be made. The effect is not dependent on particular lighting conditions, making the method more robust and more suitable for remote sensing applications. By using data representative of at least part of a spectrum of a time-varying value of a combination of pixel values at at least a number of the image points, a large amount of noise can be eliminated. This allows one to use images that are obtained by capturing light reflected off a living subject. Such images can be obtained with a relatively cheap camera or sensor array. By contrast, if one were to determine the spectrum of each pixel individually and then cluster the values of the peaks, one would have to use images obtained using a very sensitive imaging device, e.g. a passive thermal imaging device.

Also this vital sign detection can be used for detecting and thus distinguishing different subjects on the basis of vital signs is provided, comprising the steps of: detecting radiation from a field of view and providing image data from the field of view, defining image sections in the image data and detecting movement pattern in the different image sections, identifying vital signs in the different image sections on the basis of the movement pattern, and detecting the different subjects in the field of view on the basis of a spatial separation of the image sections or of groups of the image sections in which the vital signs are identified.

Identifying different subjects, e.g. human beings in a video sequence can be achieved based on the position of the respiration signal or heart beat signal obtained from the video sequence. The breathing motion is detected by identifying movement pattern in the image derived from the field of view. To identify the position of the respiration signals, the image data is divided in different image sections, which are separately analyzed and from which movement pattern are determined. The different subjects in the field of view are identified on the basis of a spatial separation of those image sections in which vital signs are identified. In other words if the vital signs which are detected at different image sections separated from each other with a respective distance, the signs are identified as vital signs from different subjects in the field of view. Since the present apparatus and the present method is merely based on the identification of movement pattern and not based on background segmentation or based on contour identification of the persons to be measured, the apparatus and the method can be used with a high flexibility and provide a reliable identification of different persons in the field of view

DETAILED DESCRIPTION OF THE EMBODIMENTS

Figure 1:
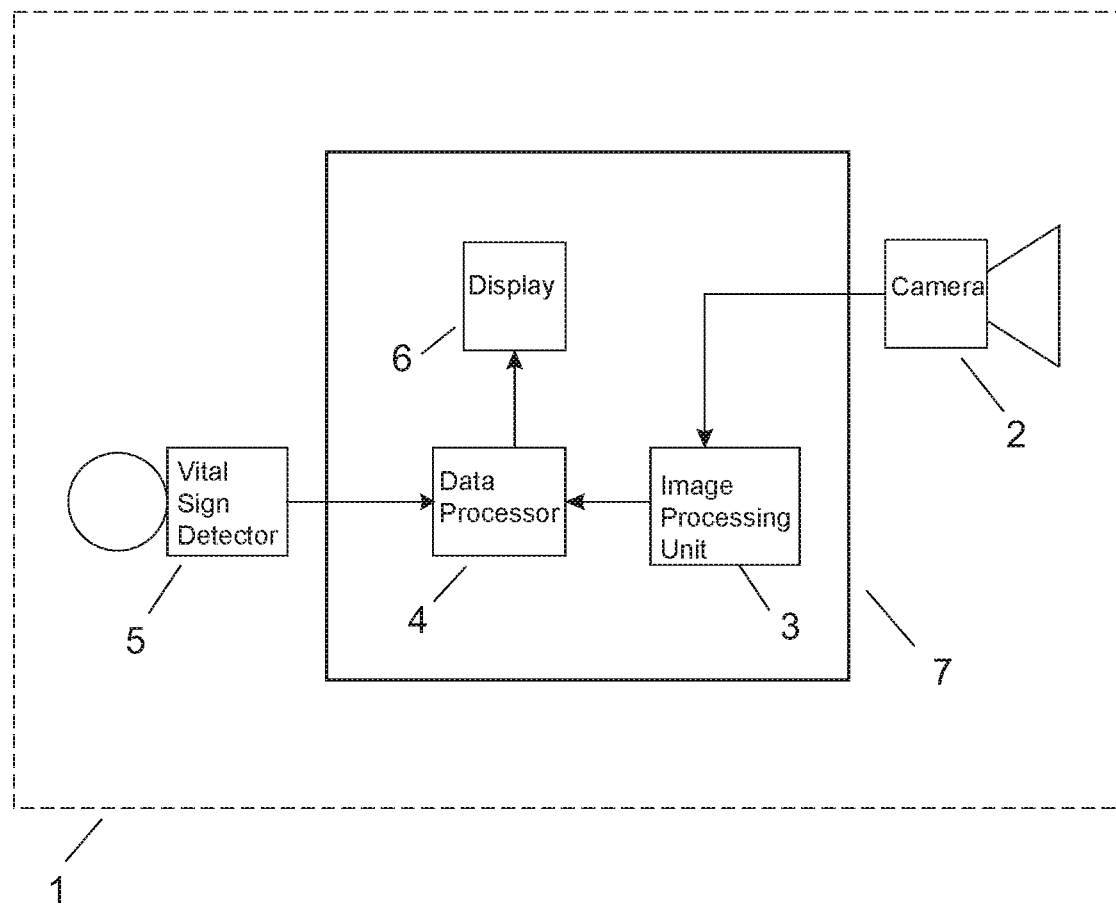
FIG. 1 shows a cardiopulmonary resuscitation assistance device.

FIG. 1 shows a cardiopulmonary resuscitation assistance device 1 for use by a rescuer when administering cardiopulmonary resuscitation to a patient, the cardiopulmonary resuscitation assistance device 1 comprises a patient facing camera 2. The patient facing camera 2 is used to capture images of the patient's chest area, including the area where the rescuer is to depress the patient's chest. The patient facing camera 2 sends the captured images to the image processing unit 3 which arranged to distinguish image subsections in the images provided by the patient facing camera 2. Some of the image subsections will comprise the rescuer's bare hands. Other image subsections will comprise the patient's chest area. If the chest area is covered by clothing only the image subsections with vital signs will be image subsection representing the rescuers bare body parts, which in case of the patient facing camera 2 facing the patient's chest will be the rescuer's hands performing cardiopulmonary resuscitation. This can be verified by matching the vital sign information obtained from the rescuer vital sign detector 5 with the vital signs obtained from the image subsections. The image subsections representing the rescuer's hands can then be used to determine the chest compression depth. For this, for example cameras that provide the depth for each image section have become available. Other techniques may be employed to obtain the same depth information per image subsection. If the patient's chest area is bare there will be both image subsections representing the patient's chest and image subsections representing the rescuer's hands. In that case rescuer vital sign information obtained from the rescuer's vital sign detector 5 is used to match the vital signs detected from the image subsections with the vital signs detected by the rescuer's vital sign detector 5. The chest compression depth is in that case derived only from those image subsections whose vital sign information match the vital sign information derived from the rescuer vital sign detector 5, thus ensuring that only the rescuer's hands are taken into consideration when determining the chest compression depth. A display 6 is used to provide cardiopulmonary resuscitation information based on the derived patient chest compression depth to the rescuer to ensure that the rescuer applies the correct chest compression depth when applying cardiopulmonary resuscitation. The chest compression depth is determined by the difference between the minimum and the maximum depth determined from the selected image subsection that represents the rescuer's hands. The frequency of the chest compression, which is also very important for applying correct cardiopulmonary resuscitation, can be determined from the variation in time of the chest compression depth of the selected image subsection representing the rescuer's hands.

The rescuer vital sign detector 5 can be as simple as a pulse meter clipped to an ear or a wrist. Alternatively the vital signs can be derived from a rescuer facing camera, for instance mounted on a headset, or positioned on the ground next to the rescuer, and extracting the vital signs from the images as described above and in a fashion corresponding to the detection of the vital sign information using the patient facing camera. It is to be noted that in case of using a rescuer facing camera as a rescuer vital sign detector the captured images can be either handled by a separate image processing unit (not shown) or by the image processing unit 3 already present, thus using the image processing unit 3 for both the patient facing camera and the rescuer facing camera.

The image processing unit 3 is arranged to distinguish an image subsection comprising the rescuer's hands from an image subsections comprising patient body parts by matching vital sign information derived from image subsections with the rescuer vital sign information derived from the rescuer vital sign detector.

The image processing unit 3, data processor 4 and display 6 are typically combined in a base unit 7 to which the patient facing camera 2 and the rescuer vital sign detector are attached wired or wirelessly as external devices.

Figure 2:
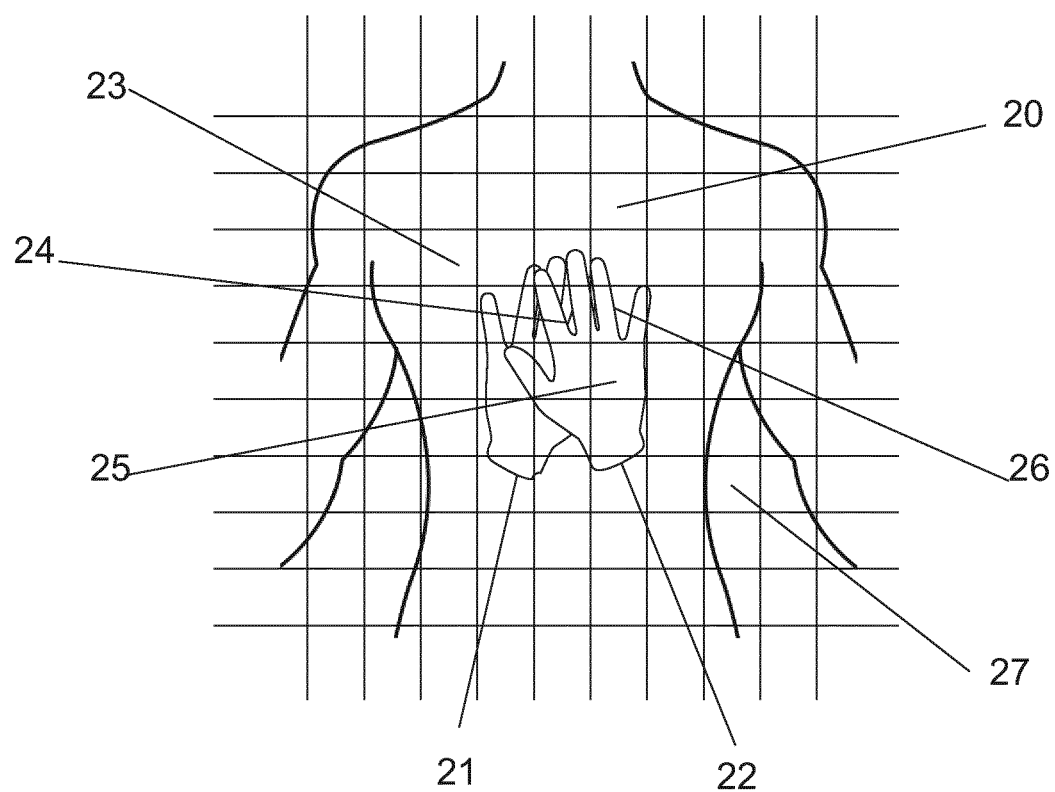
FIG. 2 shows an image in which the body part to be distinguished is a hand of the rescuer on the chest of a patient.

FIG. 2 shows an image in which the body part to be distinguished is a hand of the rescuer on the chest of a patient.

The patient's chest 20 in this example is bare, i.e many image subsections will have the vital sign information of the patient.

On the patient's chest the two hands 21, 22 of the rescuer are shown. As can be seen it might be difficult or error prone to distinguish the rescuer's hands because the shape is obscured because of the typical overlap of the hands or recommended interlocking of the fingers (not shown) as this would require image recognition software that would have to deal with subtle differences in skin color to extract the shapes to be used for recognition. By dividing the captured image of the patient's chest into many image subsections 23, 24, 25, 26, 27 and applying vital sign detection to these image subsections 23, 24, 25, 26, 27 each individual image subsection 23, 24, 25, 26, 27 can be assigned to a category. The various categories are:

an image subsection with no vital signs present 27 an image subsection with only rescuer vital signs present 24, 25 an image subsection with only patient vital signs present 23 an image subsection with both patient and rescuer vital signs present 26

The image processor can after extracting the vital sign information per subsection determine to which category they belong and subsequently select that image subsection with only rescuer vital signs present. In addition to ensure the correct representation of the chest compression depth, within the set of image subsections that contain only the vital sign information of the rescue an image subsection is chosen that has the largest depth variations as determined by the patient facing camera as this represents the correct patient chest compression depth. The images subsection dimension can be chosen to be sufficiently small to yield at least one image subsection with only the rescuer's vital sign information present. This way the number of image subsections to be processed can be reduced if required.

Figure 3:
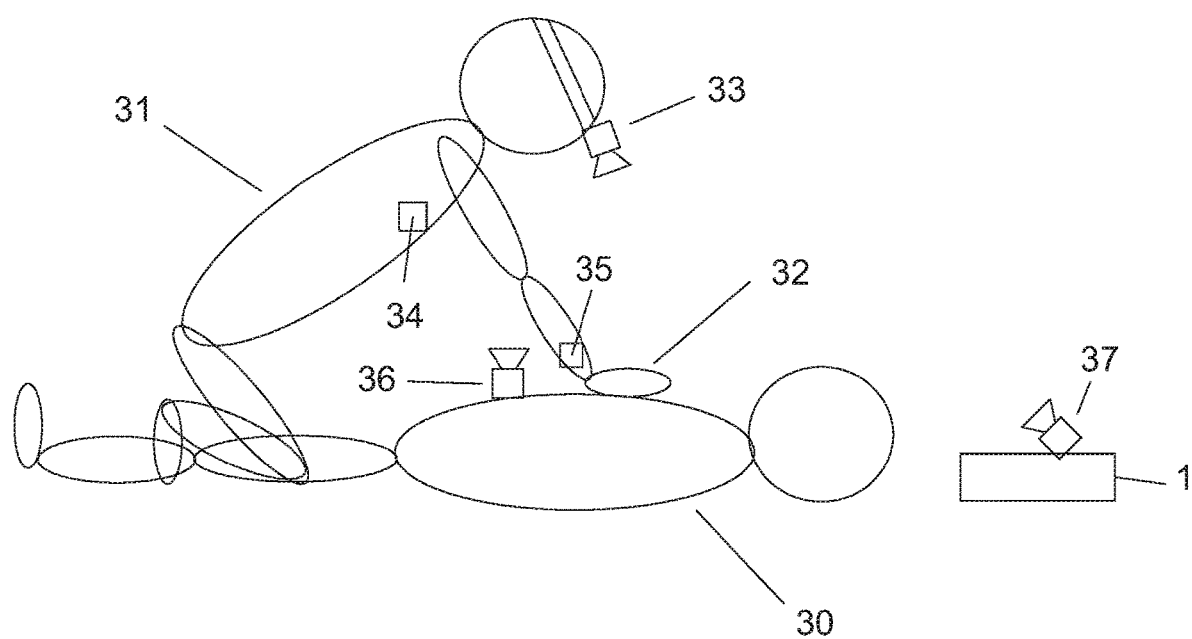
FIG. 3 shows a system having a rescuer facing camera and other options of detecting the rescuer's vital sign information.

FIG. 3 shows a system having a rescuer facing camera and other options of detecting the rescuer's vital sign information.

The patient 30 is lying on the ground, while the rescuer 31 is kneeling over the patient 30 and applying the pulsating pressure to the chest of the patient 30 using his hands 32. The rescuer 31 is wearing a patient facing camera 33, in the case shown worn on his head but other locations are possible such as the patient facing camera being worn on the rescuer's chest or positioned off the rescuer's body at a stationary position with the patient's chest in view, for instance when installed above a hospital bed. The rescuer' vital sign detector 34, 35, 36, 37 can take several forms and corresponding positions. A heart rate detector 34, 35 can be a chest worn heart rate detector 34 or a wrist worn heart rate detector 35 or integrated into the head worn patient facing camera 35 as part of the rear of the camera body that is pressed against the rescuer's head or a separate vital sign detector pressed against the rescuer's head by the strap holding the patient facing camera on the rescuer's head.

If the rescuer's vital sign detector takes the form of a rescuer facing camera, it can be a separate rescuer facing camera 36 positioned on the patient. Alternatively it can be a separate rescuer facing camera 37 sitting besides the patient and rescuer, facing the rescuer allowing the rescuer's bare body parts to be in view of the rescuer facing camera 36, 37. The rescuer facing camera can be integrated into the cardiopulmonary resuscitation assistance device 1 which then can be either positioned on the ground next to the rescuer and patient as shown, or positioned at the belly of the patient to allow the rescuer a good view of the instruction assisting the cardiopulmonary resuscitation. As the rescuer has a good view of the cardiopulmonary resuscitation assistance device's display a camera is being mounted in the cardiopulmonary resuscitation assistance device 1 next to the display, ensuring that the rescuer's head is in view of the rescuer facing camera.

As the rescuer's head might not be stationary during the administering of cardiopulmonary resuscitation to the patient but bobbing up and down while applying the pressure to the patient's chest, a head mounted patient facing camera 33 can yield inaccurate results. A rescuer facing camera 36, 37 positioned off the rescuer's body can be used to compensate for this movement by determining the variations of the distance between the rescuer facing camera 36. 37 and the rescuer's head. When the rescuer facing camera is attached to the rescuer's head, stationary objects within the view of the camera can be used to estimate the variations in the distance between the rescuer facing camera and the stationary object by determining variations in the amount and direction of movement of the rescuer's head (and thus of the patient facing camera, whose movement is to be compensated) and the cardiopulmonary resuscitation assistance device 1 can use this information to calculate the patient chest compression depth and frequency more accurately.

The invention claimed is:

1. A cardiopulmonary resuscitation assistance device for use by a Rescuer device when administering cardiopulmonary resuscitation to a patient, the cardiopulmonary resuscitation assistance device comprising a patient facing camera, an image processing unit arranged to distinguish an image subsection in images provided by the patient facing camera comprising a rescuer body part, a data processor arranged to derive patient chest compression depth from the distinguished image subsection by determining a variation of a distance measurement between the camera and the image subsection performed by the camera, and a display arranged to provide cardiopulmonary resuscitation information based on the derived patient chest compression depth to the rescuer characterized in that the cardiopulmonary resuscitation assistance device further comprises a rescuer vital signs detector and that the data processor is arranged to derive a rescuer vital sign information from the rescuer vital sign detector, and whereby the image processing unit is arranged to distinguish the image subsection from images captured by the patient facing camera comprising the rescuer body part by matching the vital sign information derived from the image subsections with rescuer vital sign information derived from the rescuer vital sign detector.

2. The cardiopulmonary resuscitation assistance device as claimed in claim 1, where the rescuer body part to be distinguished is a hand of the rescuer.

3. The cardiopulmonary resuscitation assistance device as claimed in claim 1, where the image processing unit is further arranged to determine the chest compression depth using the distinguished body part of the rescuer by determining variations in a distance measurement between the patient facing camera and the distinguished body part of the rescuer.

4. The cardiopulmonary resuscitation assistance device as claimed in claim 1,
where the rescuer vital sign detector is a rescuer facing camera,
and where the image processing unit is arranged to derive the rescuer vital sign information from the images provided by the rescuer facing camera.

5. The cardiopulmonary resuscitation assistance device as claimed in claim 3,
where the image processing unit is arranged to correct the chest compression depth using variations of an additional depth information between the patient facing camera and a stationary object in view of the patient facing camera obtained from images from a rescuer facing camera.

6. The cardiopulmonary resuscitation assistance device as claimed in claim 5,
where the depth information obtained from images from the rescuer facing camera is derived by estimating a variation of a distance between the Rescuer facing camera and the stationary object within view of the rescuer facing camera.

7. The cardiopulmonary resuscitation assistance device as claimed in claim 5,
where rescuer facing camera is a stationary camera and the depth information obtained from images from the rescuer facing camera is derived by estimating a distance between the rescuer facing camera and a head of the rescuer.

8. A method for assisting a rescuer device when administering cardiopulmonary resuscitation to a patient, the method comprising the steps of
obtaining images of the patient's chest using a patient facing camera,
processing the obtained images to distinguish an image subsection comprising a rescuer body part,
deriving patient chest compression depth from the distinguished image subsection by determining a variation in a distance measurement between the camera and the image subsection performed by the patient facing camera, and
displaying cardiopulmonary resuscitation information based on the derived patient chest compression depth to the rescuer characterized in that the method further comprises the steps of
detecting rescuer vital sign information using a rescuer vital sign detector,
distinguish the image subsection from the images captured by the patient facing camera comprising the rescuer body part by matching the vital sign information derived from the image subsection with rescuer vital sign information.

9. The method for assisting the rescuer device when administering cardiopulmonary resuscitation to the patient as claimed in claim 8,
where the rescuer body part to be distinguished is a hand of the rescuer.

10. The method for assisting the rescuer device when administering cardiopulmonary resuscitation to the patient as claimed in claim 8,
where the method comprises the step of determining the chest compression depth using the distinguished body part of the rescuer using variations in additional depth information between the patient facing camera and a stationary object in view of the patient facing camera obtained from images from a rescuer facing camera that is the rescuer vital sign detector.

11. The method for assisting the rescuer device when administering cardiopulmonary resuscitation to the patient as claimed in claim 8,
where the rescuer vital sign information is derived from images provided by a rescuer facing camera.

12. The method for assisting the rescuer device when administering cardiopulmonary resuscitation to the patient as claimed in claim 10,
where the method comprises the step of correcting the chest compression depth using a variation in an additional depth information obtained from the images from the rescuer facing camera.

13. The method for assisting the rescuer device when administering cardiopulmonary resuscitation to the patient as claimed in claim 12,
where the depth information obtained from the images from the rescuer facing camera is derived by estimating a distance between the rescuer facing camera and the stationary object within view of the rescuer facing camera.

14. The method for assisting a rescuer device when administering cardiopulmonary resuscitation to the patient as claimed in claim 12,
where rescuer facing camera is a stationary camera and the depth information obtained from images from the rescuer facing camera is derived by estimating a distance between the rescuer facing camera and a head of the rescuer.

* * * * *